(12) United States Patent
Giannetti et al.

(10) Patent No.: US 8,353,953 B2
(45) Date of Patent: Jan. 15, 2013

(54) DEVICE FOR THE IN SITU DELIVERY OF HEART VALVES

(75) Inventors: Arnaldo Giannetti, Crescentino (IT); Laura Ghione, Turin (IT); Paolo Gaschino, Castagneto Po-Turin (IT); Giovanni Righini, Chivasso (IT)

(73) Assignee: Sorin Biomedica Cardio, S.r.l., Saluggia (Vercelli) (IT)

( * ) Notice: Subject to any disclaimer, the term of this patent is extended or adjusted under 35 U.S.C. 154(b) by 309 days.

(21) Appl. No.: 12/465,278

(22) Filed: May 13, 2009

(65) Prior Publication Data
US 2010/0292784 A1 Nov. 18, 2010

(51) Int. Cl.
*A61F 2/24* (2006.01)
(52) U.S. Cl. ..................................... 623/2.11
(58) Field of Classification Search .............. 623/1.12, 623/2.11, 1.11, 1.24, 1.23, 1.26, 2.17, 2.18, 623/902, 23.68, 2.38; 606/194, 192, 108, 606/200; 604/171, 523, 524, 527; 600/433, 600/434, 144, 146, 147, 149, 150, 139
See application file for complete search history.

(56) References Cited

U.S. PATENT DOCUMENTS

| 3,671,979 A | 6/1972 | Moulopoulos |
| 4,011,947 A | 3/1977 | Sawyer |
| 4,056,854 A | 11/1977 | Boretos et al. |
| 4,477,930 A | 10/1984 | Totten et al. |
| 4,601,706 A | 7/1986 | Aillon |
| 4,624,822 A | 11/1986 | Arru et al. |
| 4,684,364 A | 8/1987 | Sawyer et al. |
| 4,722,725 A | 2/1988 | Sawyer et al. |
| 4,732,152 A | 3/1988 | Wallsten et al. |
| 4,758,151 A | 7/1988 | Arru et al. |
| 4,777,951 A | 10/1988 | Cribier et al. |
| 4,784,644 A | 11/1988 | Sawyer et al. |
| 4,994,077 A | 2/1991 | Dobben |
| 5,057,092 A * | 10/1991 | Webster, Jr. .................. 604/527 |
| 5,084,151 A | 1/1992 | Vallana et al. |
| 5,123,919 A | 6/1992 | Sauter et al. |
| 5,133,845 A | 7/1992 | Vallana et al. |
| 5,181,911 A | 1/1993 | Shturman |
| 5,201,757 A | 4/1993 | Heyn et al. |
| 5,287,848 A | 2/1994 | Cubb |
| 5,304,189 A | 4/1994 | Goldberg et al. |
| 5,332,402 A | 7/1994 | Teitelbaum |
| 5,370,684 A | 12/1994 | Vallana et al. |

(Continued)

FOREIGN PATENT DOCUMENTS
DE 19546692 C2 11/2002
(Continued)

OTHER PUBLICATIONS
European Search Report Issued in EP Application No. 09160183, dated Oct. 2, 2009, 6 pages.
(Continued)

*Primary Examiner* — Kathleen Sonnett
*Assistant Examiner* — Jocelin Tanner
(74) *Attorney, Agent, or Firm* — Faegre Baker Daniels LLP

(57) ABSTRACT

A device for deploying a cardiac valve prosthesis includes a distal valve holder portion and a shaft extending towards the valve holder portion. The shaft is selectively bendable to a curved shape to vary the spatial orientation of the valve holder portion with respect to the desired implantation site.

16 Claims, 5 Drawing Sheets

U.S. PATENT DOCUMENTS

| | | | |
|---|---|---|---|
| 5,370,685 A | 12/1994 | Stevens | |
| 5,387,247 A | 2/1995 | Vallana et al. | |
| 5,397,351 A | 3/1995 | Pavcnik et al. | |
| 5,411,552 A | 5/1995 | Andersen et al. | |
| 5,423,886 A | 6/1995 | Arru et al. | |
| 5,433,723 A | 7/1995 | Lindenberg et al. | |
| 5,445,646 A | 8/1995 | Euteneuer et al. | |
| 5,545,214 A | 8/1996 | Stevens | |
| 5,554,185 A | 9/1996 | Block et al. | |
| 5,556,414 A | 9/1996 | Turi | |
| 5,662,712 A | 9/1997 | Pathak et al. | |
| 5,693,083 A | 12/1997 | Baker et al. | |
| 5,766,151 A | 6/1998 | Valley et al. | |
| 5,772,693 A | 6/1998 | Brownlee | |
| 5,782,811 A * | 7/1998 | Samson et al. | 604/527 |
| 5,824,064 A | 10/1998 | Taheri | |
| 5,840,081 A | 11/1998 | Andersen et al. | |
| 5,849,005 A | 12/1998 | Garrison et al. | |
| 5,855,597 A | 1/1999 | Jayaraman | |
| 5,855,601 A | 1/1999 | Bessler et al. | |
| 5,871,489 A | 2/1999 | Ovil | |
| 5,925,063 A | 7/1999 | Khosravi | |
| 5,951,600 A | 9/1999 | Lemelson | |
| 5,954,766 A | 9/1999 | Zadno-Azizi et al. | |
| 5,957,949 A | 9/1999 | Leonhardt et al. | |
| 5,980,570 A | 11/1999 | Simpson | |
| 6,010,530 A | 1/2000 | Goicoechea | |
| 6,010,531 A | 1/2000 | Donlon et al. | |
| 6,029,671 A | 2/2000 | Stevens et al. | |
| 6,030,360 A * | 2/2000 | Biggs | 604/95.01 |
| 6,090,099 A * | 7/2000 | Samson et al. | 604/527 |
| 6,106,497 A | 8/2000 | Wang | |
| 6,125,852 A | 10/2000 | Stevens et al. | |
| 6,139,572 A | 10/2000 | Campbell et al. | |
| 6,168,614 B1 | 1/2001 | Andersen et al. | |
| 6,251,093 B1 | 6/2001 | Valley et al. | |
| 6,299,638 B1 | 10/2001 | Sauter | |
| 6,309,382 B1 | 10/2001 | Garrison et al. | |
| 6,346,071 B1 | 2/2002 | Mussivand | |
| 6,402,780 B2 | 6/2002 | Williamson, IV et al. | |
| 6,416,474 B1 | 7/2002 | Penner et al. | |
| 6,425,916 B1 | 7/2002 | Garrison et al. | |
| 6,454,799 B1 | 9/2002 | Schreck | |
| 6,458,153 B1 | 10/2002 | Bailey et al. | |
| 6,482,228 B1 | 11/2002 | Norred | |
| 6,572,642 B2 | 6/2003 | Rinaldi et al. | |
| 6,582,462 B1 | 6/2003 | Andersen et al. | |
| 6,607,553 B1 | 8/2003 | Healy et al. | |
| 6,641,558 B1 | 11/2003 | Aboul-Hosn et al. | |
| 6,645,197 B2 | 11/2003 | Garrison et al. | |
| 6,652,578 B2 | 11/2003 | Bailey et al. | |
| 6,685,739 B2 | 2/2004 | DiMatteo et al. | |
| 6,726,648 B2 | 4/2004 | Kaplon et al. | |
| 6,726,712 B1 | 4/2004 | Raeder-Devens et al. | |
| 6,730,118 B2 | 5/2004 | Spenser et al. | |
| 6,733,525 B2 | 5/2004 | Yang et al. | |
| 6,767,362 B2 | 7/2004 | Schreck | |
| 6,769,434 B2 | 8/2004 | Liddicoat et al. | |
| 6,805,711 B2 | 10/2004 | Quijano et al. | |
| 6,830,584 B1 | 12/2004 | Seguin | |
| 6,830,585 B1 | 12/2004 | Artof et al. | |
| 6,875,231 B2 | 4/2005 | Anduiza et al. | |
| 6,893,460 B2 | 5/2005 | Spenser et al. | |
| 6,908,481 B2 | 6/2005 | Cribier | |
| 6,913,618 B2 | 7/2005 | Denardo et al. | |
| 6,945,957 B2 | 9/2005 | Freyman | |
| 6,964,673 B2 | 11/2005 | Tsugita et al. | |
| 6,974,464 B2 | 12/2005 | Quijano et al. | |
| 6,981,942 B2 | 1/2006 | Khaw et al. | |
| 6,991,646 B2 | 1/2006 | Clerc et al. | |
| 7,001,423 B2 | 2/2006 | Euteneuer et al. | |
| 7,018,406 B2 | 3/2006 | Seguin et al. | |
| 7,018,408 B2 | 3/2006 | Bailey et al. | |
| 7,041,132 B2 | 5/2006 | Quijano et al. | |
| 7,044,966 B2 | 5/2006 | Svanidze et al. | |
| 7,077,801 B2 | 7/2006 | Haverich | |
| 7,101,396 B2 | 9/2006 | Artof et al. | |
| 7,144,364 B2 | 12/2006 | Barbut et al. | |
| 7,156,872 B2 | 1/2007 | Strecker | |
| 7,195,641 B2 | 3/2007 | Palmaz et al. | |
| 7,201,761 B2 | 4/2007 | Woolfson et al. | |
| 7,329,279 B2 | 2/2008 | Haug et al. | |
| 7,338,467 B2 | 3/2008 | Lutter | |
| 7,338,520 B2 | 3/2008 | Bailey et al. | |
| 7,374,571 B2 | 5/2008 | Pease et al. | |
| RE40,377 E | 6/2008 | Williamson, IV et al. | |
| 7,399,315 B2 | 7/2008 | Iobbi | |
| 7,544,206 B2 | 6/2009 | Cohn | |
| 7,556,646 B2 | 7/2009 | Yang et al. | |
| 7,591,843 B1 | 9/2009 | Escano et al. | |
| 7,618,432 B2 | 11/2009 | Pedersen et al. | |
| 7,708,775 B2 | 5/2010 | Rowe et al. | |
| 7,993,392 B2 | 8/2011 | Righini et al. | |
| 8,057,539 B2 | 11/2011 | Ghione et al. | |
| 8,070,799 B2 | 12/2011 | Righini et al. | |
| 8,114,154 B2 | 2/2012 | Righini et al. | |
| 2001/0002445 A1 | 5/2001 | Vesely | |
| 2001/0007956 A1 | 7/2001 | Letac et al. | |
| 2001/0010017 A1 | 7/2001 | Letac et al. | |
| 2001/0039450 A1 | 11/2001 | Pavcnik et al. | |
| 2001/0044591 A1 | 11/2001 | Stevens et al. | |
| 2002/0029075 A1 | 3/2002 | Leonhardt | |
| 2002/0042651 A1 | 4/2002 | Liddicoat et al. | |
| 2002/0045846 A1 | 4/2002 | Kaplon et al. | |
| 2002/0058995 A1 | 5/2002 | Stevens | |
| 2002/0099431 A1 | 7/2002 | Armstrong et al. | |
| 2002/0107531 A1 | 8/2002 | Schreck et al. | |
| 2002/0117264 A1 | 8/2002 | Rinaldi et al. | |
| 2002/0123802 A1 * | 9/2002 | Snyders | 623/2.18 |
| 2002/0138138 A1 | 9/2002 | Yang | |
| 2002/0151970 A1 | 10/2002 | Garrison et al. | |
| 2002/0198594 A1 | 12/2002 | Schreck | |
| 2003/0014104 A1 | 1/2003 | Cribier | |
| 2003/0023300 A1 | 1/2003 | Bailey et al. | |
| 2003/0023303 A1 | 1/2003 | Palmaz et al. | |
| 2003/0033000 A1 | 2/2003 | DiCaprio et al. | |
| 2003/0036795 A1 | 2/2003 | Andersen et al. | |
| 2003/0055495 A1 | 3/2003 | Pease et al. | |
| 2003/0109924 A1 | 6/2003 | Cribier | |
| 2003/0130729 A1 | 7/2003 | Paniagua et al. | |
| 2003/0153974 A1 | 8/2003 | Spenser et al. | |
| 2003/0163194 A1 | 8/2003 | Quijano et al. | |
| 2003/0191521 A1 | 10/2003 | Denardo et al. | |
| 2003/0191528 A1 | 10/2003 | Quijano et al. | |
| 2004/0034411 A1 | 2/2004 | Quijano et al. | |
| 2004/0039371 A1 * | 2/2004 | Tockman et al. | 604/528 |
| 2004/0039436 A1 | 2/2004 | Spenser et al. | |
| 2004/0039442 A1 | 2/2004 | St. Goar et al. | |
| 2004/0049266 A1 | 3/2004 | Anduiza et al. | |
| 2004/0055606 A1 | 3/2004 | Hendricksen et al. | |
| 2004/0078072 A1 | 4/2004 | Tu et al. | |
| 2004/0093060 A1 | 5/2004 | Seguin et al. | |
| 2004/0093063 A1 | 5/2004 | Wright et al. | |
| 2004/0106976 A1 | 6/2004 | Bailey et al. | |
| 2004/0127848 A1 | 7/2004 | Freyman | |
| 2004/0147993 A1 | 7/2004 | Westlund et al. | |
| 2004/0186563 A1 | 9/2004 | Lobbi | |
| 2004/0215333 A1 | 10/2004 | Duran et al. | |
| 2004/0236170 A1 | 11/2004 | Kim | |
| 2004/0249413 A1 | 12/2004 | Allen et al. | |
| 2005/0075584 A1 | 4/2005 | Cali | |
| 2005/0075712 A1 | 4/2005 | Biancucci et al. | |
| 2005/0075713 A1 | 4/2005 | Biancucci et al. | |
| 2005/0075717 A1 | 4/2005 | Nguyen et al. | |
| 2005/0075718 A1 | 4/2005 | Nguyen et al. | |
| 2005/0075719 A1 | 4/2005 | Bergheim | |
| 2005/0075720 A1 | 4/2005 | Nguyen et al. | |
| 2005/0075724 A1 | 4/2005 | Svanidze et al. | |
| 2005/0075726 A1 | 4/2005 | Svanidze et al. | |
| 2005/0075728 A1 | 4/2005 | Nguyen et al. | |
| 2005/0075729 A1 | 4/2005 | Nguyen et al. | |
| 2005/0075730 A1 | 4/2005 | Myers et al. | |
| 2005/0075731 A1 | 4/2005 | Artof et al. | |
| 2005/0080476 A1 | 4/2005 | Gunderson et al. | |
| 2005/0096993 A1 | 5/2005 | Pradhan et al. | |
| 2005/0104957 A1 | 5/2005 | Okamoto et al. | |
| 2005/0137686 A1 | 6/2005 | Salahieh et al. | |

| | | |
|---|---|---|
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143809 A1 | 6/2005 | Salahieh et al. |
| 2005/0165480 A1 | 7/2005 | Jordan et al. |
| 2005/0197695 A1 | 9/2005 | Stacchino et al. |
| 2005/0240200 A1 | 10/2005 | Bergheim |
| 2005/0251251 A1 | 11/2005 | Cribier |
| 2005/0267493 A1 | 12/2005 | Schreck et al. |
| 2006/0004436 A1 | 1/2006 | Amarant et al. |
| 2006/0004439 A1 | 1/2006 | Spenser et al. |
| 2006/0020333 A1 | 1/2006 | Lashinski et al. |
| 2006/0020334 A1* | 1/2006 | Lashinski et al. ............ 623/2.11 |
| 2006/0025844 A1 | 2/2006 | Majercak et al. |
| 2006/0030922 A1 | 2/2006 | Dolan |
| 2006/0063199 A1 | 3/2006 | Elgebaly et al. |
| 2006/0064054 A1* | 3/2006 | Sakakine et al. ........... 604/95.04 |
| 2006/0074271 A1 | 4/2006 | Cotter |
| 2006/0074484 A1 | 4/2006 | Huber |
| 2006/0085060 A1 | 4/2006 | Campbell |
| 2006/0095025 A1 | 5/2006 | Levine et al. |
| 2006/0100639 A1 | 5/2006 | Levin et al. |
| 2006/0135962 A1 | 6/2006 | Kick et al. |
| 2006/0142838 A1 | 6/2006 | Molaei et al. |
| 2006/0142848 A1 | 6/2006 | Gabbay |
| 2006/0178740 A1 | 8/2006 | Stacchino et al. |
| 2006/0195134 A1 | 8/2006 | Crittenden |
| 2006/0195184 A1 | 8/2006 | Lane et al. |
| 2006/0229659 A1 | 10/2006 | Gifford et al. |
| 2006/0241656 A1 | 10/2006 | Starksen et al. |
| 2006/0271081 A1 | 11/2006 | Realyvasquez |
| 2006/0276775 A1 | 12/2006 | Rosenberg et al. |
| 2007/0010850 A1 | 1/2007 | Balgobin et al. |
| 2007/0027534 A1 | 2/2007 | Bergheim et al. |
| 2007/0032850 A1 | 2/2007 | Ruiz et al. |
| 2007/0055357 A1 | 3/2007 | Pokorney et al. |
| 2007/0088431 A1 | 4/2007 | Bourang et al. |
| 2007/0100302 A1 | 5/2007 | Dicarlo et al. |
| 2007/0100356 A1 | 5/2007 | Lucatero et al. |
| 2007/0100440 A1 | 5/2007 | Figulla et al. |
| 2007/0112355 A1 | 5/2007 | Salahieh et al. |
| 2007/0112422 A1 | 5/2007 | Dehdashtian |
| 2007/0118207 A1 | 5/2007 | Amplatz et al. |
| 2007/0118209 A1 | 5/2007 | Strecker |
| 2007/0156225 A1 | 7/2007 | George et al. |
| 2007/0162100 A1 | 7/2007 | Gabbay |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0162113 A1 | 7/2007 | Sharkawy et al. |
| 2007/0173861 A1 | 7/2007 | Chu |
| 2007/0203503 A1 | 8/2007 | Salahieh et al. |
| 2007/0203561 A1 | 8/2007 | Forster et al. |
| 2007/0203575 A1 | 8/2007 | Forster et al. |
| 2007/0219630 A1 | 9/2007 | Chu |
| 2007/0250097 A1 | 10/2007 | Weitzner et al. |
| 2007/0265702 A1 | 11/2007 | Lattouf |
| 2008/0021546 A1 | 1/2008 | Patz et al. |
| 2008/0065011 A1 | 3/2008 | Marchand et al. |
| 2008/0082165 A1 | 4/2008 | Wilson et al. |
| 2008/0097595 A1 | 4/2008 | Gabbay |
| 2008/0140189 A1 | 6/2008 | Nguyen et al. |
| 2008/0147160 A1 | 6/2008 | Ghione et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0147188 A1 | 6/2008 | Steinberg |
| 2008/0183097 A1 | 7/2008 | Leyde et al. |
| 2008/0208216 A1 | 8/2008 | Cerier |
| 2008/0262507 A1 | 10/2008 | Righini et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0069890 A1 | 3/2009 | Suri et al. |
| 2009/0105794 A1 | 4/2009 | Ziarno et al. |
| 2009/0118580 A1 | 5/2009 | Sun et al. |
| 2009/0157174 A1 | 6/2009 | Yoganathan et al. |
| 2009/0164004 A1 | 6/2009 | Cohn |
| 2009/0164006 A1 | 6/2009 | Seguin et al. |
| 2009/0171363 A1 | 7/2009 | Chocron |
| 2009/0171456 A1 | 7/2009 | Kveen et al. |
| 2009/0177275 A1 | 7/2009 | Case |
| 2009/0228093 A1 | 9/2009 | Taylor et al. |
| 2009/0234443 A1 | 9/2009 | Ottma et al. |
| 2009/0240326 A1 | 9/2009 | Wilson et al. |
| 2009/0254165 A1 | 10/2009 | Tabor et al. |
| 2009/0281609 A1 | 11/2009 | Benichou et al. |
| 2009/0281619 A1 | 11/2009 | Le et al. |
| 2010/0191326 A1* | 7/2010 | Alkhatib ...................... 623/2.11 |
| 2010/0292782 A1 | 11/2010 | Giannetti |
| 2010/0292783 A1 | 11/2010 | Giannetti |
| 2012/0053684 A1 | 3/2012 | Righini |

FOREIGN PATENT DOCUMENTS

| | | |
|---|---|---|
| DE | 19857887 B4 | 5/2005 |
| EP | 133420 B1 | 2/1988 |
| EP | 0155245 B1 | 5/1990 |
| EP | 0592410 B1 | 10/1995 |
| EP | 0512359 B1 | 12/1996 |
| EP | 0515324 B1 | 12/1996 |
| EP | 0850607 A1 | 7/1998 |
| EP | 1057460 A1 | 12/2000 |
| EP | 1356763 A2 | 10/2003 |
| EP | 1356793 A2 | 10/2003 |
| EP | 0852481 B1 | 2/2004 |
| EP | 1440671 A2 | 7/2004 |
| EP | 1088529 B1 | 6/2005 |
| EP | 955895 B1 | 8/2005 |
| EP | 1488735 B1 | 6/2007 |
| EP | 1212989 B1 | 1/2008 |
| EP | 1653884 B1 | 6/2008 |
| EP | 1935377 A1 | 6/2008 |
| EP | 1955643 A1 | 8/2008 |
| EP | 1570809 B1 | 1/2009 |
| EP | 2033581 A1 | 3/2009 |
| EP | 2033597 A1 | 3/2009 |
| FR | 2828091 A1 | 2/2003 |
| WO | WO 97/24989 A1 | 7/1997 |
| WO | WO 98/17202 A1 | 4/1998 |
| WO | WO 98/29057 A1 | 7/1998 |
| WO | WO 99/04728 A1 | 2/1999 |
| WO | WO 99/56665 A1 | 11/1999 |
| WO | WO 00/18303 A1 | 4/2000 |
| WO | WO 00/41525 A2 | 7/2000 |
| WO | WO 00/41652 A1 | 7/2000 |
| WO | WO 01/21244 A1 | 3/2001 |
| WO | WO 01/62189 A1 | 8/2001 |
| WO | WO 01/64137 A1 | 9/2001 |
| WO | WO 01/76510 A2 | 10/2001 |
| WO | WO 02/41789 A2 | 5/2002 |
| WO | WO 02/47575 A2 | 6/2002 |
| WO | WO 02/076348 A1 | 10/2002 |
| WO | WO 03/003943 A3 | 11/2003 |
| WO | WO 03/094797 A1 | 11/2003 |
| WO | WO 2004/089253 A1 | 10/2004 |
| WO | WO 2005/046525 A1 | 5/2005 |
| WO | WO 2005/065200 A2 | 7/2005 |
| WO | WO 2005/096993 A1 | 10/2005 |
| WO | WO 2005/104957 A2 | 11/2005 |
| WO | WO 2006/054107 A2 | 5/2006 |
| WO | WO 2006/063199 A2 | 6/2006 |
| WO | WO 2006/086135 A2 | 8/2006 |
| WO | WO 2006/116558 A2 | 11/2006 |
| WO | WO 2006/135551 A2 | 12/2006 |
| WO | WO 2006/138173 A2 | 12/2006 |
| WO | WO 2007/071436 A2 | 6/2007 |

| WO | WO 2007/076463 A2 | 7/2007 |
| WO | WO 2008/097589 A1 | 8/2008 |
| WO | WO 2008/125153 A1 | 10/2008 |

OTHER PUBLICATIONS

European Search Report Issued in EP Application No. 09160186, dated Oct. 6, 2009, 5 pages.
European Search Report Issued in EP Application No. 07115951, dated Sep. 24, 2009, 8 pages.
Extended European Search Report issued in EP Application 06126552, dated Jun. 6, 2007, 7 pages.
Extended European Search Report issued in EP Application 06126556, dated Jul. 6, 2007, 13 pages.
Extended European Search Report Issued in EP Application 07115960, dated Jan. 24, 2008, 8 pages.
Extended European Search Report issued in EP Application 09158822, dated Sep. 9, 2009, 5 pages.
Ho, Paul C., "Percutaneous aortic valve replacement: A novel design of the delivery and deployment system", Minimally Invasive Therapy, 2008; 17:3; 190-194.
Huber, Christoph H. et al., "Direct-Access Valve Replacement: A Novel Approach for Off-Pump Valve Implantation Using Valved Stents", Journal of the American College of Cardiology, vol. 46, No. 2, 2005, pp. 366-370.
Partial European Search Report issued in EP App No. 06126556, mailed Apr. 16, 2007, 6 pages.
European Search Report and Search Opinion of European Patent Application No. 07115960.2, dated Jan. 24, 2008.
European Search Report issued in EP Application 08163752, dated Dec. 29, 2008.
European Search Report Issued in EP 09160184 dated Oct. 22, 2009.
European Search Report issued in EP Application No. 08159301, mailed Dec. 30, 2008, 6 pages.
Partial European Search Report issued in EP Application No. 10155332, dated Jun. 9, 2011, 7 pages.

\* cited by examiner

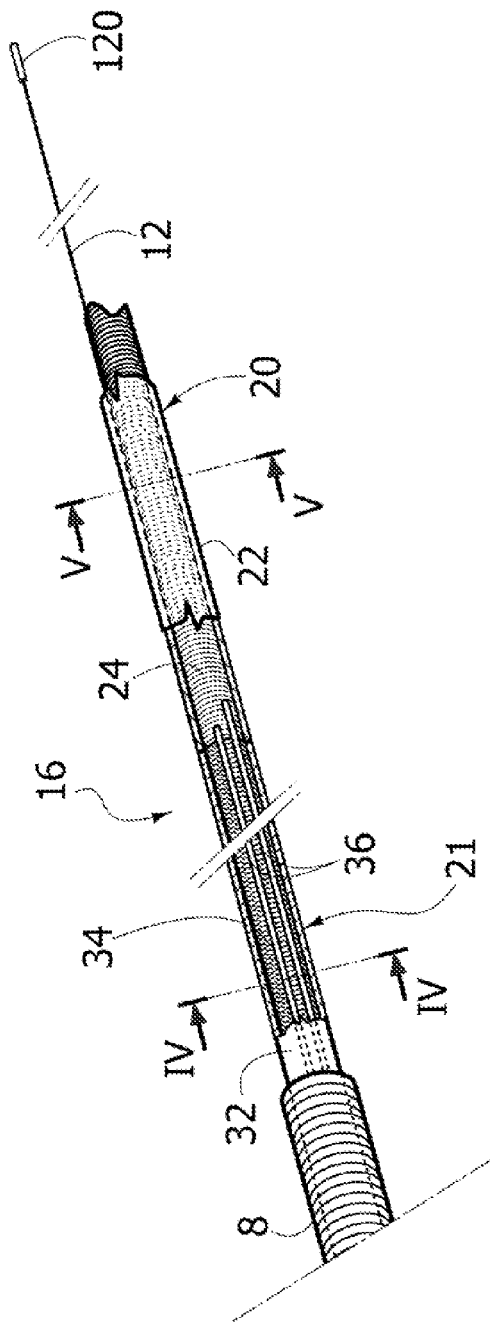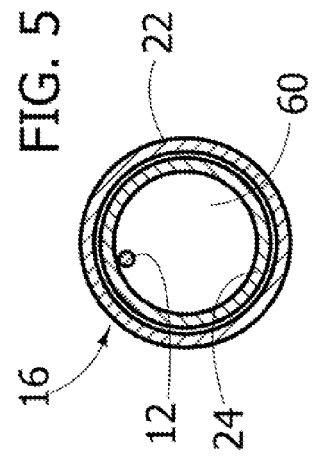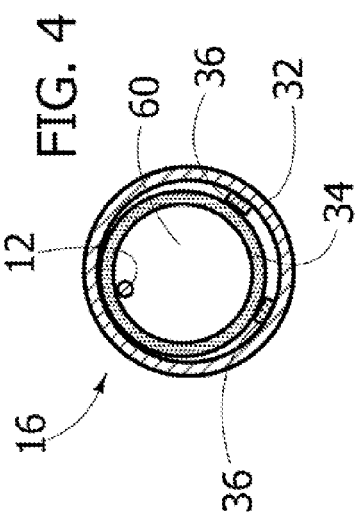

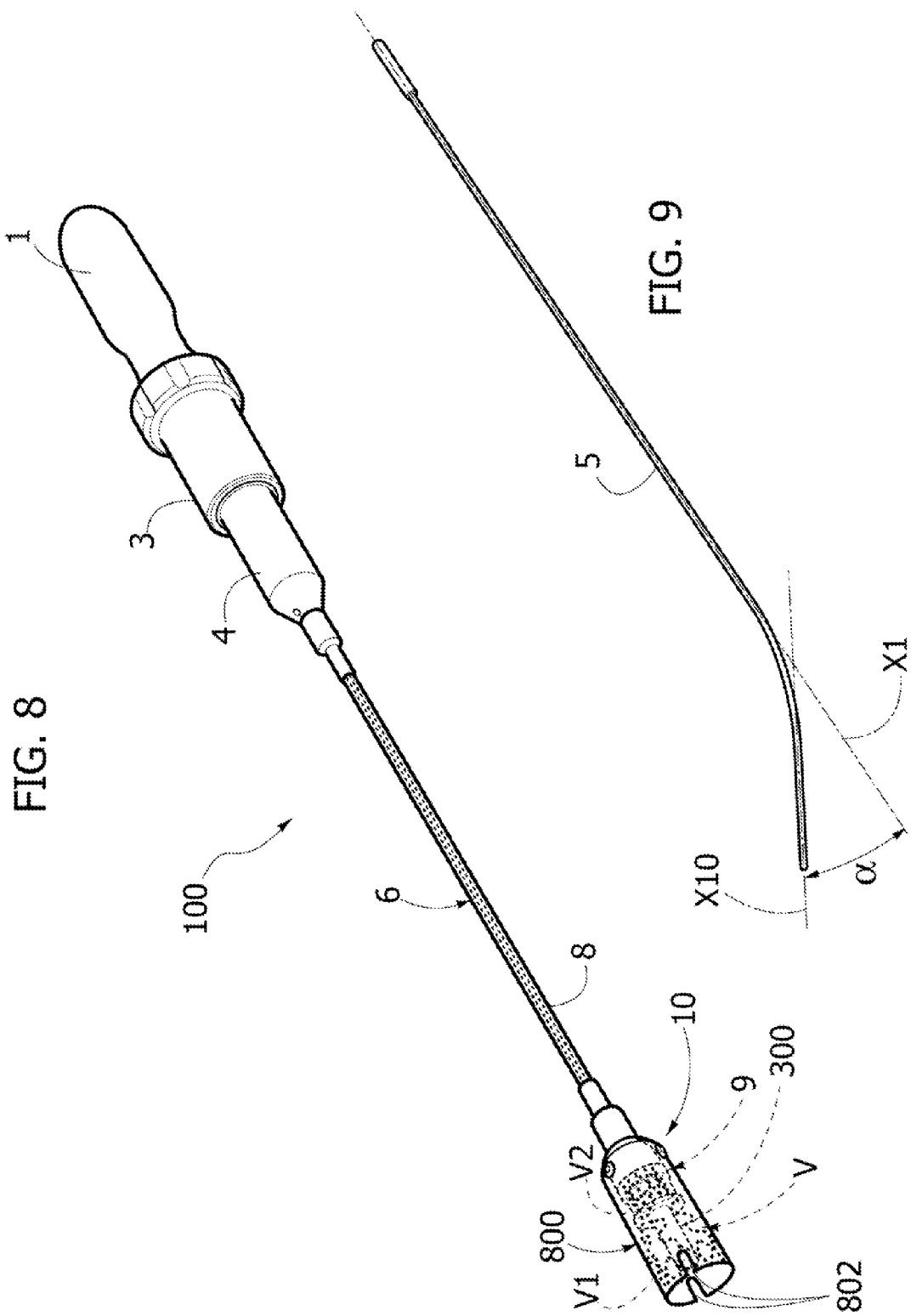

DEVICE FOR THE IN SITU DELIVERY OF HEART VALVES

TECHNICAL FIELD

The present invention relates to devices for the in situ delivery of heart valves. More specifically, the invention relates to delivery devices for cardiac valve prostheses using minimally-invasive surgical techniques or endovascular delivery techniques.

BACKGROUND

Expandable prosthetic valves typically include an expandable and collapsible anchoring structure or armature, which is able to support and fix the valve prosthesis in the implantation position, and prosthetic valve elements, generally in the form of leaflets or flaps, which are stably connected to the anchoring structure and are able to regulate blood flow.

These expandable prosthetic valves enable implantation using various minimally invasive or sutureless techniques. Exemplary applications for such an expandable valve prosthesis include aortic and pulmonary valve replacement. Various techniques are generally known for implanting an aortic valve prosthesis and include percutaneous implantation (e.g., transvascular delivery), dissection of the ascending aorta using minimally invasive thoracic access (e.g., mini-thoracotomy or mini-sternotomy), and transapical delivery wherein the aortic valve annulus is accessed through an opening near the apex of the left ventricle. The percutaneous and thoracic access approaches involve delivering the prosthesis in a direction opposing blood flow (i.e., retrograde), whereas the transapical approach involves delivering the prosthesis in the same direction as blood flow (i.e., antegrade).

SUMMARY

The present invention, according to one embodiment, is a device for delivering a cardiac valve prosthesis to an implantation site. The device includes a distal valve holder portion defining a cavity adapted to receive and radially constrain the valve prosthesis therein; a shaft coupled to the valve holder portion, the shaft including a tubular sleeve and a core disposed partially within the tubular sleeve, the core adapted to move axially with respect to the sleeve; a valve support disposed at or near a distal end of the shaft, the valve support including an annular recess adapted to mate with a portion of the valve prosthesis; a deployment mechanism adapted to axially translate the valve support with respect to the distal valve holder, such that the valve prosthesis is selectively deployed at the implantation site; and a deflection mechanism coupled to shaft, the deflection mechanism adapted to selectively vary the spatial orientation of the valve holder portion with respect to the implantation site.

The present invention, according to another embodiment, is a device for delivering a cardiac valve prosthesis to an implantation site, which includes a distal valve holder portion and a shaft coupled to the valve holder portion. The shaft is selectively bendable to a curved shape to selectively vary the spatial orientation of the valve holder portion with respect to the implantation site.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 2a and 2b show an exploded view, wherein the components shown in FIG. 2b are intended to be located within the components shown in FIG. 2a.

FIG. 3 is a partial sectional view of some of a portion of the device shown in FIG. 2.

FIG. 4 is a cross-sectional view taken along line IV-IV of FIG. 3.

FIG. 5 is a cross-sectional view taken along line V-V of FIG. 3.

FIG. 8 is a perspective view of a valve delivery device according to another exemplary embodiment.

FIG. 9 is a perspective view of an exemplary component of an embodiment.

Figure 1:
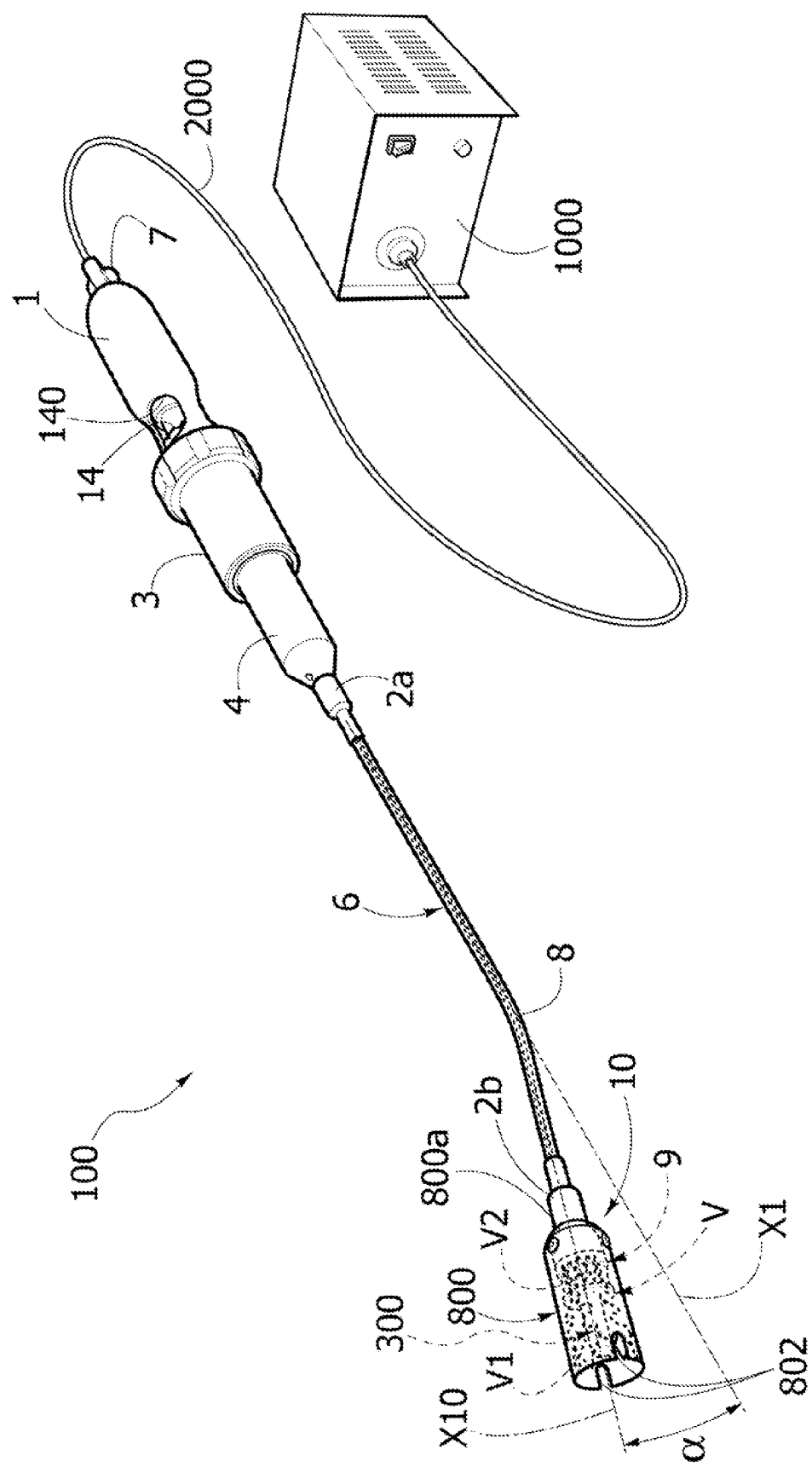
FIG. 1 is a general perspective view of a valve delivery device according to an exemplary embodiment.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

In the following description, numerous specific details are given to provide a thorough understanding of embodiments. The embodiments can be practiced without one or more of the specific details, or with other methods, components, materials, etc. Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

FIGS. 1 and 8 are perspective views of exemplary embodiments of a valve delivery device 100. The device 100 includes a handle 1 for manipulation by a practitioner and a holder unit 10 for a valve V to be delivered. As shown, the handle 1 and the holder unit 10 are generally located at proximal and distal ends of the device 100.

As used herein, "proximal" and "distal" refer to the conditions of handling of the device 100 by a practitioner who manipulates the device via the handle 1 at the "proximal" end in order to permit delivery of the valve V at the "distal" end of the device 100. Thus "proximal" and "distal," as used herein, have no direct relationship to the approach (retrograde or antegrade) adopted for delivering the valve V.

In one exemplary embodiment, the valve V is of the type disclosed in U.S. Publication 2006/0178740, which is incorporated herein by reference. Such a prosthetic valve includes two annular end portions V1, V2 (i.e. inflow and outflow with respect to the direction of unimpeded flow of blood through the valve).

As shown in FIG. 1, the valve is arranged in the holder unit 10 at the distal delivery end of the device 100 with the annular portions V1, V2 in a radially contracted condition.

In the exemplary illustrated arrangement, the annular portions V1 and V2 are located "distally" and "proximally," respectively of each other with reference to the orientation of the device 100. In the following it will be assumed that the valve V is delivered by releasing the annular portion V1 first and then by causing the valve V to gradually expand (e.g. due to its elastic or superelastic nature), starting from the portion V1 and continuing to the portion V2, until expansion is complete.

As further shown in FIG. 1, the device 100 includes a shaft 6, which is adapted to be selectively shaped into a curved pattern as further described below. The shaft 6 extends from the handle 1 to the holder unit 10 for the valve.

Figure 2:
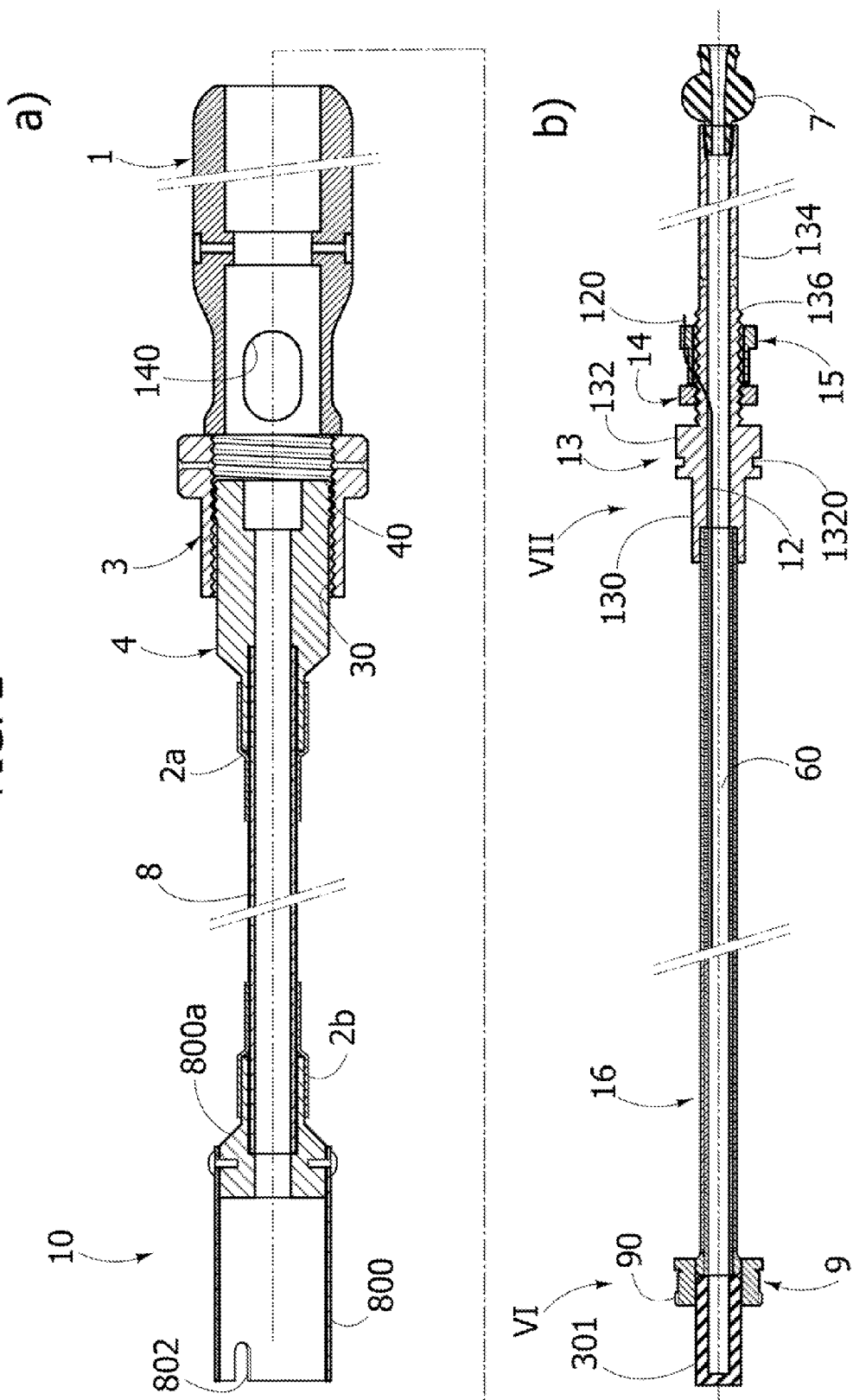
FIGS. 2a and 2b are longitudinal sectional views of the device of FIG. 1 according to exemplary embodiments.
Figure 6:
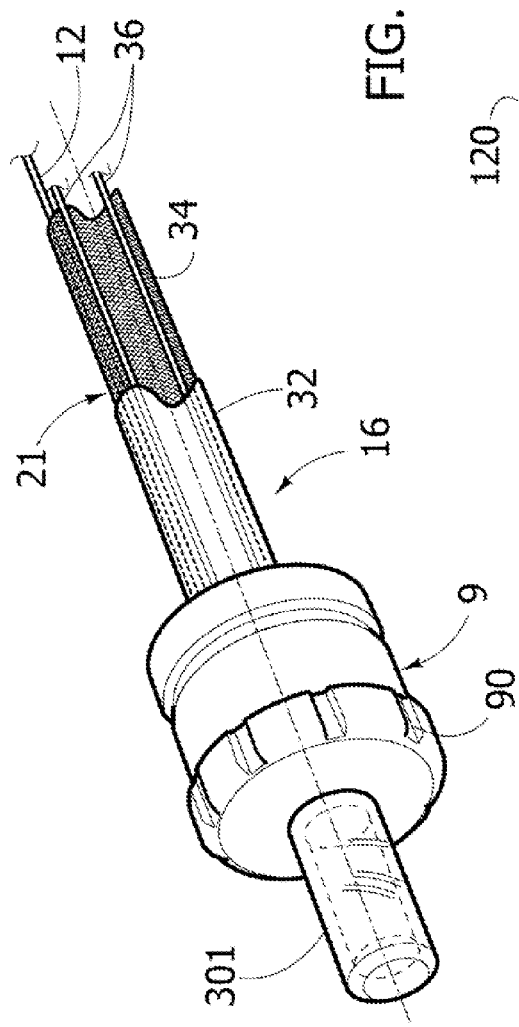
FIG. 6 is a perspective view showing a portion of the device indicated by an arrow VI in FIG. 2b.

In various embodiments, the holder unit 10 includes an inner body or valve support 9 integral with or coupled to the tubular core 16 and including an annular groove or similar recessed 90 formation (see FIGS. 2b) adapted to receive the (proximal) annular portion V2 of the valve V in a radially contracted condition.

In the embodiments shown in FIGS. 2 to 7, the shaft 6 includes a tubular sheath or sleeve 8 slidably arranged over the tubular core 16. The sleeve 8 is adapted to couple with or fit into a proximal sleeve 4, fixed in rotation with respect to the handle 1. The sleeve 4 has an outer threaded surface 40 to cooperate with a complementary threaded formation 30 provided at the inner surface of a tubular rotary actuation member 3 arranged around the sleeve 4. The actuation member 3 is fixed in translation with respect to the shaft 6. In an embodiment, a tapered sheath 2a acts as an interface between the proximal sleeve 4 and the sleeve 8.

The sleeve 8 extends over the tubular core 16 and terminates with a distal portion including a terminal enlarged portion 800 adapted to extend around the distal portion of the core 16 to form an external tubular member of the holder unit 10, which is adapted to radially constrain and retain the valve V when disposed therein.

The terminal enlarged portion 800 may be either one-piece with the rest of the sleeve 8 or, as shown in FIG. 2a, may include a separate tubular member coupled (e.g., adhesively or by means of screws, rivets, protrusions, etc.) to a funnel-shaped formation 800a located at the terminal end of the distal portion 80 of the sleeve 8. In an embodiment, a tapered sheath 2b acts as an interface between the sleeve 8 and the funnel shaped element 800a.

According to various embodiments, the threaded surface/formations 30, 40 comprise a "micrometric" device actuatable by rotating the actuation member 3 to produce and precisely control axial displacement of the sleeve 8, 800 over the core 16. Such a controlled movement may take place along the core 16 starting from an extended position, as shown in FIG. 1, where the outer member 800 of the holder unit 10 radially constrains and retains the valve V.

As the sleeves 4, 8 are gradually retracted towards the handle 1 (by operation of the actuation device 30, 40, which are controlled by the rotary member 3), the outer member 800 gradually releases first the annular portion V1 of the valve V, then the portion of the valve located between the annular portion V1 and the annular portion V2, and finally the annular portion V2 of the valve V, thus permitting gradual radial expansion of the valve V. According to other embodiments, the device 100 includes a two-part actuation mechanism of the type disclosed in co-pending, commonly assigned U.S. application 12/465,262, now published as U.S. 2010/0292782, filed on May 13, 2009, entitled "DEVICE FOR THE IN SITU DELIVERY OF HEART VALVES," which is incorporated herein by reference.

In an exemplary delivery procedure of the valve V, the practitioner introduces the device 100 into the patient's body and advances it through the delivery route or path until the outer member 800 is located at the annulus of the natural valve to be substituted by the valve V. The practitioner may use any of a variety of known techniques for delivering the device 100 to the valve annulus site.

In various embodiments, the radial dimensions of portion 800 are slightly less than the radial dimensions of the annulus of the natural valve intended to be substituted. In these embodiments, the outer member 800 will not unduly move about or "dance," while being positioned within the natural annulus. In various exemplary embodiments, these radial dimensions are in the range of between about 10 mm and about 27 mm.

In the exemplary case of aortic valve replacement, this may involve the outer member 800 being located immediately distally (with respect to the flow direction blood pumped from the left heart ventricle) of the aortic annulus so that the annular portions V1 and V2 are located on opposite sides (i.e. astride) of the Valsalva sinuses. In other words, the portion V1 is located on one of the ventricle side and the aortic root side of the Valsalva sinuses, and the portion V2 is located on the opposite side of the Valsalva sinuses.

Once the portion 800 is disposed properly at the annulus site, the practitioner will actuate the rotary actuation member 30 by rotating it in such a way that cooperation of the threaded sections 30 and 40 will cause the outer sleeve 8 and the proximal sleeve 4 to start gradually retracting towards the handle 1. As a result of this retraction of the outer sleeve, the outer member 800 will gradually disengage the annular portion V1 of the valve V. The annular portion V1 will thus be allowed to radially expand.

Gradual withdrawal of the sleeves 4, 8 proceeds until the outer member 800 has almost completely disengaged the valve V, while the annular formation V2 is still securely retained by the tubular member 800 of which still forces the annular formation V2 of the valve within the inner body 9 of the a holder portion.

This deployment mechanism of the annular formation V1 and the valve V may be controlled very precisely by the practitioner via the screw-like mechanism 30, 40 actuated by the rotary member 3. Deployment may take place in a gradual and easily controllable manner by enabling the practitioner to verify how deployment proceeds.

Also, so long as the annular formation V2 of the valve V is still constrained within the formation 9 by the tubular member 800, the practitioner still retains firm control of the partially (e.g., "basket-like") expanded valve V. The practitioner will thus be able to adjust the position of the valve V both axially and radially, that is by rotating the valve V around its longitudinal axis, e.g. to ensure that radially expanding anchoring formations of the valve V are precisely aligned with the Valsalva sinuses to firmly and reliably retain in place the valve V once finally delivered.

In various embodiments, the portion 800 has a marginal outer edge provided with one or more notches 802 providing a reference in angular positioning of the valve V at the implantation site. In various embodiments, these notches are visible during implantation (e.g., using radiography or other common implantation techniques).

According to various embodiment, the annular portion V2 of the valve V is received in the formation 9 and is thus blocked against any significant axial movement, during the retraction of the sleeve 8 and the sleeve 4 over the core 16. In other words, the valve V will not experience any significant axial displacement with respect to the shaft 6. The retraction of the outer sleeve 8 continues until the annular formation V2 (and the valve V as a whole) become disengaged from the device 100 and thus completely deployed at the implantation site.

While a cardiac valve prosthesis including two self-expandable annular portions has been considered herein for exemplary purposes, this disclosure similarly applied to cardiac valve prostheses including further expandable annular portions and/or one or more annular portions that are expandable via an expansion means such as an inflatable balloon.

In various embodiments, the device 100 includes an illuminator device 300 located at the holder unit 10 to provide illumination of the implantation site of the valve V. In minimally-invasive surgical procedures the operation site is observed directly by the practitioner via the (minimally-invasive) access path gained through the thorax of the patient. The action of the illuminator 300 is beneficial in that penetration of ambience light to the implantation site may be reduced or impeded by the body structures of the patient. In various embodiments, the illuminator device 300 is adjustable.

In the exemplary embodiment shown in FIG. 1, the illuminator 300 is fed with light radiation produced by a source 1000 via fiber optical element 2000 which extends through the shaft 6 (for instance by extending in an axial cavity 60 provided in the tubular core 16). Preferably (see also FIG. 2b), the fiber optical element 2000 enters the shaft 6 by means of a connector 7 (e.g, a Luer-Lock female connector). In other embodiments, such an axial cavity 60 of the shaft 6 may be also be employed for other reasons as detailed below.

Various embodiments include features to facilitate spatial orientation of the valve V with respect to the implantation site. In various embodiments, the shaft 6 is flexible and adapted to be imparted specific curved shapes. The shaft 6 being flexible and selectively bendable makes it possible to deflect or "steer" the holder unit 10 with respect to the handle 1. Due to such delectability or steerability the practitioner can select a desired spatial orientation of the holder unit 10 (and thus of the valve V) which facilitates positioning the valve V at the implantation site with a desired spatial orientation. This orientation may correspond to an orientation that avoids or minimizes the application of undesired mechanical stresses to the implantation site (i.e. to the heart tissues of the patient), while achieving the desired orientation of the valve V.

Steerability of the holder unit 10 permits a main axis X10 of the holder unit 10 to be arranged at a desired orientation which is generally skew or bent with respect to the axis X1 of the proximal portion of the device. The axis X1 essentially corresponds to the main axis of the handle 1 and the parts of the device adjacent thereto (i.e. the proximal sleeve 4 and the rotary actuation member 3). FIG. 1 is exemplary of the main axis X10 of the holder portion 10 being steered (i.e. bent) to an angle α with respect to the axis X1.

It will likewise be appreciated that any desired "radial" or "polar" orientation of the axis X10 with respect to the axis X1 may be simply achieved by the practitioner by rotating the device 100, as a whole, around the axis X1, by rotating the handle 1 within the practitioner's hand.

Figure 7:
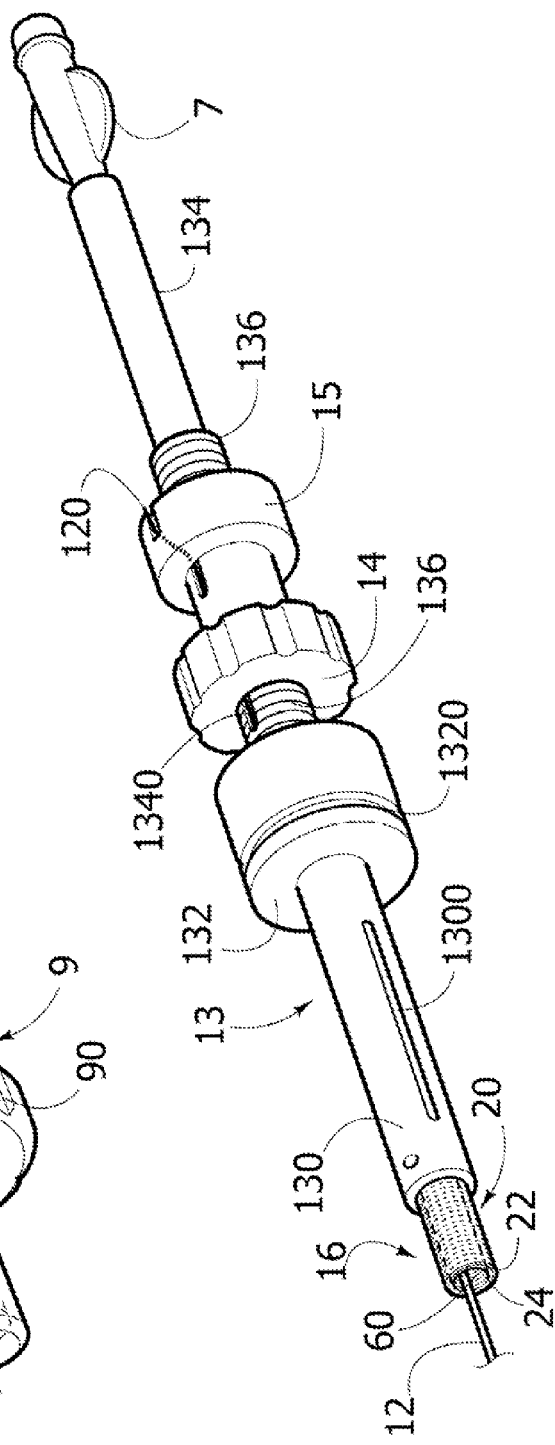
FIG. 7 is a perspective view showing a portion of the device indicated by an arrow VII in FIG. 2b.

In various embodiments, the shaft 6 is made adjustable or "steerable" by means of a wire member 12 extending through the axial cavity 60 in the tubular core 16 and cooperating with a tensioning mechanism (see FIG. 7). In an embodiment, the tensioning mechanism includes a fixed tubular member 13, a rotary member 14 and an anchoring member 15.

The tubular member 13 includes a distal end 130 coupled and integral with a proximal end of the core 16, a radially expanded portion 132 and a proximal portion 134 provided with an outer thread 136.

The rotary element 14 is coupled to the outer thread 136 by means of an inner thread. The second tubular element 15 is slidably mounted over the outer thread 136 of the member 13 and is fixed in rotation (e.g., by means of a radial pin engaging a groove provided in the member 13).

The wire member 12 is anchored at the distal portion of the core 16 (e.g. in proximity of the inner body 9 carrying the annular portion 90 into which the portion V2 of the valve V is constrained) and extends within the shaft towards the mechanism 13, 14, 15.

With reference to FIGS. 2a, 2b, in some embodiments, the actuation mechanism 13, 14, 15 extends through the proximal sleeve 4, the rotary actuation member 3 and the handle 1. The distal portion 30 of the actuation mechanism may also extend partially into the sleeve 8 and the core 16. In some embodiments, the distal portion 130 is inserted in the sleeve 4 with the radially expanded portion 132 providing an abutment surface to the sleeve 4.

Moreover, in various embodiments, the member 13 is provided with a longitudinal groove 1300 (see FIG. 7) adapted to rotationally fix the sleeve 4 with respect to the member 13 (e.g., by means of a radial pin or screw). In these embodiments, the length of the groove 1300 determines the longitudinal (i.e., axial) range of relative motion of the member 13 with respect to the sleeve 4. In other embodiments, the expanded portion 132 has an annular groove 1320, which is adapted to fix the rotating actuation member 3 in translation with respect to the member 13 (e.g., by means of a radial pin or screw engaging groove 1320), which allowing partial or complete rotational movement therein.

In various embodiments, the radially expanded portion 132, which is surrounded by the rotary actuation member 3 and the outer thread 136, as well as the whole proximal portion 134, is located inside the handle 1. In various embodiments, the member 13 has an elongated shape permitting it to extend within the handle 1 to be secured thereto (e.g., by means of radial screws), while also acting as a support member for the shaft 6. This ensures no rotation of the member 13 inside the device 100, since the handle 1 is firmly held by the practitioner's hand.

The mechanism 13, 14, 15 is intended to pull (i.e., to apply a longitudinal, tensile force to) the wire member 12 towards the handle 1 so that a longitudinal tensile force is applied to the core 16 to produce controlled bending of the shaft 6.

In various embodiments, the core 16 includes a proximal portion 20 and a distal portion 21. The proximal portion 20 (see, e.g., FIG. 3) includes an external sheath 22 and a coil element 24, helically wound therein. The coil element 24 is intended to provide a certain amount of flexibility to the core 16 (i.e., to the shaft 6), particularly to the proximal portion 20.

The distal portion 21 (see, e.g., FIG. 6) includes an external sheath 32 and a braided tubular element 34 located therein. A pair of longitudinal formations 36 is constrained between the external sheath 32 and the braided tubular element 34, and partially extends also between the coil element 24 and external sheath 24 of the proximal portion 20. In some embodiments, the longitudinal formations 36 are made of metallic material. The longitudinal formations 36 are intended to give a certain amount of stiffness to the distal portion 21 of the shaft 6, avoiding at the same time any undesired lateral bending thereof.

The coil element 24 and the braided tubular element 34 define an axial cavity, such as, for instance, the axial cavity 60, wherein the wire 12 extends from the distal portion of the core 6 to the member 15, where a proximal portion 120 of the wire member 12 is securely fixed.

In various embodiments, the wire 12 includes a proximal portion 120 which passes through a slot 1340 provided in the member 13 (see FIG. 7) and is anchored (for instance by mechanical clamping or crimping) to the member 15. In various embodiments, the wire 12 may be a tendon, a string, a suture, a wire, or a variety of other elements adapted to transmit a tensile force.

In various embodiments, the member 14 is a rotary ring-like member. Rotating the member 14 will thus cause the element 15 to slide axially relative to the member 1 in either direction depending on the direction the member 14 is rotated.

When rotated, the member 14 moves longitudinally in a proximal or distal direction, depending on the direction of rotation, along the outer thread 136 of member 13, thereby producing displacement of the member 15 over the member 13, proximally or distally depending on the direction of rotation of member 14.

In the case of a displacement of the member 14 in the proximal direction (i.e., towards or into the handle 1), the element 15 will be urged proximally to produce/increase longitudinal tensioning of the wire-like member 12, which, in turn, will translate into (increased) bending of the shaft 6.

In the case of a displacement of the member 14 in the distal direction (i.e., away or outwardly of the handle 1), the member 15 will correspondingly be able to slide distally thus releasing the tensile force on the wire-like element 12. This will gradually release its longitudinal tension, thereby reducing the amount of bending between the axes X10 and X1. The members 14, 15 will remain in contact with each other as long as there is a longitudinal tension in the wire-like element 12, acting as a sort of bias on members 14, 15. This ensures correspondence between the displacements of members 14 and 15 (i.e., smooth adjustment of the amount of bending). The amount of bending (i.e., the resulting angle a between the axes X10 and X1 in FIG. 1) can thus be selectively adjusted by the practitioner by acting on the rotary member 14.

In the embodiments considered herein the distal portion 21 of the tubular core 16 is intended to achieve the desired amount of bending with respect to the axis X1 having a minimum flexibility, while the proximal portion 20 is given a certain amount of flexibility substantially without being angularly displaced from the axis X1.

In various embodiments, the handle 1 is provided with an opening or window 140 through which the rotary member 14 can be actuated by the practitioner (e.g., by alternate action of the thumb). This exemplary mechanism provides the benefit of being actuatable by the practitioner by rotating the rotary member 14 while retaining a firm hold of the handle 1.

Rotation can be, as previously described, in either direction, so that the amount of longitudinal tension applied on the member 12 can be selectively varied while the bending angle of the shaft 6 will correspondingly vary based an the amount of tension applied by the member 12. The angle between the axes X10 and X1 (i.e. the spatial orientation of the holder portion 10 and the valve V located therein) can thus be selectively varied depending on the practitioner's needs and preferences during the intervention.

Those skilled in the art will appreciate that the action of applying a longitudinal tension onto the member 12 can be achieved by resorting to different mechanisms (e.g., by means of screw mechanism actuated by rotating the handle 1).

The embodiment of FIGS. 8 and 9 may adopt, insofar as the release/delivery mechanism of the valve V is concerned, the same "micrometric" mechanism actuated via the rotary member 3 as discussed above. In the embodiments of FIGS. 8 and 9, the desired "steering" of the holder portion 10, causing the angle X10 to form an adjustable angle α to the axis X1, can be achieved by coupling to the shaft a shaping member 5 (see FIG. 9) such as, for instance, a wire-like shaping member 5 inserted into an axial cavity of the shaft 6. In various embodiments, such a cavity may be the cavity 60 already provided for the fiber optic element 2000 to extend through the core 16 (as shown, e.g., in FIG. 2b).

In various embodiments, the shaping member 5 (FIG. 9) can be comprised of a bent steel rod rigid enough that, when inserted and advanced into the flexible shaft 6, the shaping member 5 will impart to the shaft 6 a bent shape which will correspond to the bent shape of the member. The composite shape of the bending member 5 and the flexible shaft 6 will depend on the bending resistance of each component.

In various embodiments, the shaping member 5 is one of an assortment of otherwise similar shaping member having different values for the "steering" angle α between X1 and X10 to be imparted to the shaft 6. Accordingly, once access to the implantation size is gained, the practitioner may evaluate the desired orientation of the holder portion 10 which will allow optimal delivery of the valve V at the implantation site. The practitioner will then select a positioning member 5 out of the assortment as the one providing such desired orientation. The shaping member thus selected will then be inserted into the shaft 6 to impart to the shaft the desired mutual orientation of the axes X10 to the axes X1.

Various modifications and additions can be made to the exemplary embodiments discussed without departing from the scope of the present invention. Accordingly, the scope of the present invention is intended to embrace all such alternatives, modifications, and variations as fall within the scope of the claims, together with all equivalents thereof.

We claim:

1. A device for delivering a cardiac valve prosthesis comprising an expandable, tissue, stented heart valve including an annular inflow portion, and annular outflow portion, and a plurality of anchoring arms, to an implantation site, the device comprising:

a distal valve holder portion defining a cavity adapted to receive and radially constrain the annular inflow portion, the annular outflow portion, and the anchoring arms of the valve prosthesis therein;

a shaft coupled to the valve holder portion, the shaft including a tubular sleeve and a core disposed partially within the tubular sleeve, the core having a proximal portion and a distal portion and the core being adapted to move axially with respect to the sleeve;

wherein the proximal portion includes an external sheath and a coil element disposed therein in order to provide flexibility to the proximal portion of the shaft, and the distal portion includes an external sheath, a braided tubular element disposed therein, and a pair of longitudinal formations constrained between the external sheath and the braided tubular element, the longitudinal formations extending partially along the shaft in the proximal portion and comprising a limited radial portion of the distal portion, and adapted to stiffen the distal portion of the shaft;

a valve support disposed at or near a distal end of the shaft, the valve support including an annular recess adapted to mate with the outflow portion of the valve prosthesis;

a deployment mechanism adapted to axially translate the valve support with respect to the distal valve holder, such that the valve prosthesis is selectively deployed at the implantation site; and a deflection mechanism coupled to shaft, the deflection mechanism adapted to selectively vary the spatial orientation of the valve holder portion with respect to the implantation site.

2. The device of claim 1, wherein the shaft is selectively bendable to a curved shape to selectively vary the spatial orientation of the valve holder portion with respect to the implantation site.

3. The device of claim 2, including a curved shaping member for coupling to the shaft to impart to the shaft a curved shape influenced by the shaping member.

4. The device of claim 3, wherein the shaft has an axial cavity for insertion of the curved shaping member.

5. The device of either of claim 4, wherein the curved shaping member is in the form of a curved rod.

6. The device of any of claim 5, wherein the curved shaping member for coupling to the shaft is selectable out of a plurality of shaping members each having a respective curved shape, whereby the shaft is imparted different curved shapes by coupling it to different shaping members in the assortment.

7. The device of claim 2, wherein the shaft is configured to bend when subjected to a longitudinal force.

8. The device of claim 7, wherein the shaft has a cavity and a wire-like member extending in the cavity, the wire-like member having associated tensioning members to apply a longitudinal force to the wire to produce a bending of the shaft.

9. The device of claim 8, wherein the tensioning members include:

a tubular member having a terminal abutment surface for the shaft;

an anchoring member for anchoring a proximal end of the wire-like member; and an actuation member actuatable between the tubular member and the anchoring member, the actuation member operable to selectively produce relative movement of the tubular member with respect to the anchoring member to thereby apply a longitudinal tensile force to the wire-like member.

10. The device of claim 8, including a rotary actuation member adapted to apply a longitudinal force to the shaft.

11. The device of claim 10, including a handle with the shaft extending from the handle, the handle including the rotary actuation member located therein and open to access from outside the handle.

12. The device of claim 11, including an opening in the handle for access to the rotary actuation member.

13. The device of claim 12, for deploying a cardiac valve prosthesis including at least one radially expandable annular portion, wherein the valve holder portion includes at least one constraint member for radially constraining the at least one annular portion, the at least one constraint member actuatable to release the at least one annular formation constrained thereby to permit radial expansion thereof.

14. The device of claim 13, wherein the at least one constraint member includes at least one sleeve slidably actuatable along the shaft, whereby the at least one constraint member releases the at least one annular formation constrained thereby.

15. The device of claim 14, wherein the distal valve holder portion has a diameter of between about 10 mm and about 27 mm.

16. The device of claim 2, wherein the distal valve holder portion has a marginal outer edge provided with at least one notch providing reference in angular positioning of the cardiac valve prosthesis.

* * * * *